US 10,661,636 B2

(12) United States Patent
Bauer et al.

(10) Patent No.: US 10,661,636 B2
(45) Date of Patent: May 26, 2020

(54) SCENTING DEVICE FOR SCENTING A VEHICLE INTERIOR

(71) Applicant: Mahle International GmbH, Stuttgart (DE)

(72) Inventors: Andre Bauer, Wendlingen (DE); Thomas Feith, Korntal-Muechingen (DE); Juergen Heilemann, Wendlingen (DE)

(73) Assignee: Mahle International GmbH (DE)

( * ) Notice: Subject to any disclaimer, the term of this patent is extended or adjusted under 35 U.S.C. 154(b) by 305 days.

(21) Appl. No.: 15/878,397

(22) Filed: Jan. 23, 2018

(65) Prior Publication Data

US 2018/0208024 A1    Jul. 26, 2018

(30) Foreign Application Priority Data

Jan. 26, 2017   (DE) ........................ 10 2017 201 238

(51) Int. Cl.
*B60H 3/00*   (2006.01)
*A61L 9/12*   (2006.01)
(Continued)

(52) U.S. Cl.
CPC .............. *B60H 3/0035* (2013.01); *A61L 9/12* (2013.01); *A61L 9/125* (2013.01); *A61L 9/127* (2013.01);
(Continued)

(58) Field of Classification Search
CPC . A61L 9/12; A61L 9/125; A61L 9/127; A61L 2209/11; A61L 2209/133;
(Continued)

(56) References Cited

U.S. PATENT DOCUMENTS 3,027,918 A * 4/1962 Robra .................... B21C 31/00
                                                              137/624.13
3,506,032 A * 4/1970 Eveleigh ............. F04B 43/1253
                                                              137/624.2
(Continued)

FOREIGN PATENT DOCUMENTS

DE    202005015709 U1    12/2005
DE    102007010796 A1    9/2008
(Continued)

OTHER PUBLICATIONS

English abstract for DE-102007010796, Sep. 2008.
English abstract for DE-10 2010 011 596, Nov. 2011.
English abstract for DE-102014227015, Jun. 2016.

*Primary Examiner* — Charles S Bushey
(74) *Attorney, Agent, or Firm* — Fishman Stewart PLLC (57) ABSTRACT

A scenting device for scenting a vehicle interior may include at least one aromatic substance container holding a supply of an aromatic substance. The device may also include a feeding duct for feeding air to the at least one aromatic substance container and a discharge duct for discharging air enriched with the aromatic substance. The device may further include at least one scenting path for enriching air with the aromatic substance from the at least one aromatic substance container. The device may include a bypass duct branching off from the feeding duct and bypassing the at least one aromatic substance container. The device may also include a bypass valve and at least one container valve. The device may include a camshaft including a bypass cam configured to actuate the bypass valve and at least one container cam configured to actuate the at least one container valve.

20 Claims, 3 Drawing Sheets

(51) Int. Cl.
*F16K 31/524* (2006.01)
*F16K 11/16* (2006.01)
*B65D 83/26* (2006.01)
*B65D 83/68* (2006.01)

(52) U.S. Cl.
CPC .......... *F16K 11/166* (2013.01); *F16K 31/524* (2013.01); *F16K 31/52416* (2013.01); *A61L 2209/11* (2013.01); *A61L 2209/133* (2013.01); *A61L 2209/134* (2013.01); *A61L 2209/16* (2013.01); *B60H 2003/0042* (2013.01); *B60H 2003/0057* (2013.01); *B65D 83/262* (2013.01); *B65D 83/682* (2013.01)

(58) Field of Classification Search
CPC ........... A61L 2209/134; A61L 2209/16; B60H 3/0035; B60H 2003/0042; B60H 2003/0057; B65D 83/262; B65D 83/682; F16K 11/166; F16K 31/524; F16K 31/52416
USPC ................ 261/44.7, 45, 46, 54, 55, DIG. 88
See application file for complete search history.

(56) References Cited

U.S. PATENT DOCUMENTS

| | | | | |
|---|---|---|---|---|
| 4,082,115 | A * | 4/1978 | Gibb | F01D 17/18 137/630.2 |
| 4,495,560 | A * | 1/1985 | Sugimoto | B60H 1/00814 700/34 |
| 5,071,621 | A * | 12/1991 | Tokuhiro | A61L 9/12 422/4 |
| 6,959,728 | B2 * | 11/2005 | McCombs | F16K 11/14 137/596.1 |
| 8,794,266 | B1 * | 8/2014 | Friedman | F16K 31/52416 137/595 |
| 2001/0022198 | A1 * | 9/2001 | Kuriyama | F16K 11/14 137/630.19 |
| 2004/0194836 | A1 * | 10/2004 | Arrowood, Jr. | F16K 11/105 137/636.1 |

FOREIGN PATENT DOCUMENTS

| | | |
|---|---|---|
| DE | 10 2008 032 883 A1 | 1/2010 |
| DE | 10 2010 011 596 A1 | 11/2011 |
| DE | 102014227015 A1 | 6/2016 |

* cited by examiner

SCENTING DEVICE FOR SCENTING A VEHICLE INTERIOR

CROSS-REFERENCE TO RELATED APPLICATIONS

This application claims priority to German Patent Application No. DE 10 2017 201 238.2, filed on Jan. 26, 2017, the contents of which are hereby incorporated by reference in its entirety.

TECHNICAL FIELD

The present invention relates to a scenting device for scenting a vehicle interior, with at least one aromatic substance container holding a supply of an aromatic substance. The invention, furthermore, relates to a vehicle with such a scenting device.

BACKGROUND

Generic scenting devices serve the purpose of scenting a vehicle interior of a vehicle. For this purpose, air enriched with aromatic substance is fed to the vehicle interior.

Such a scenting device is known from DE 10 2007 010 796 A1. The scenting device comprises an aromatic substance container holding a supply of an aromatic substance. For enriching the air to be fed to the vehicle interior with the aromatic substance from the aromatic substance container, air is delivered with a blower and conducted through the aromatic substance container. In addition, a bypass duct for conducting the air past the aromatic substance container is provided.

DE 10 2010 011 596 A1 shows a scenting device, in which a bypass duct connects a feeding duct for feeding air to the aromatic substance container and a discharge duct for discharging air enriched with aromatic substance from the scenting device, in order to create a pressure equalisation between the feeding duct and the discharge duct and thereby reduce contaminations in the feeding duct and in the discharge duct.

An intensity of the perception of the aromatic substance or an aromatic substance intensity in the air is associated in particular with the concentration of the aromatic substance in the air enriched with the aromatic substance. Here, a plurality of factors can influence the concentration of the aromatic substance in air. These include in particular the dwell time of the air in the aromatic substance container, the temperature of the air and/or of the aromatic substance and the volume flow coming into contact with the aromatic substance, in particular the flow velocity of the air.

In order to adapt the actual aromatic substance intensity to a desired aromatic substance intensity, a correction function for controlling the scenting device is proposed in DE 10 2008 032 883 A1. To this end, a blower for generating the volume flow fed to the aromatic substance container is controlled by activating and deactivating and/or by adapting the rotational speed of the blower, in order to change the volume flow.

Disadvantageous with scenting devices known from the prior art is in particular that no adaptation or only an inadequate adaptation of the aromatic substance intensity to the desires of occupants of the associated vehicle is possible.

SUMMARY

The present invention therefore deals with the object of stating improved or at least other embodiments for a scenting device of the type mentioned at the outset and for a vehicle having such a scenting device, which are characterized in particular by an increased precision of the adjustment of the aromatic substance intensity and/or an improved comfort.

According to the invention, this object is solved through the subjects of the independent claim(s). Advantageous embodiments are subject of the dependent claims.

The present invention is based on the general idea of having a cam of a camshaft interact with a valve for adjusting a volume flow of air flowing through an aromatic substance container. The interaction of the cam of the camshaft with the valve is adjustable with great precision and in principle continuously. Accordingly, the volume flow of the air flowing through the aromatic substance container, in particular the flow velocity of the air, can be adjusted with an increased accuracy. As a result, the enrichment with aromatic substance of the air flowing through the aromatic substance container and consequently the aromatic intensity in the air can be adjusted with increased precision. In addition to an improved accuracy of the scenting device, this results in a greater adjusting range in particular of the aromatic substance intensity, and/or an increased comfort for users of the scenting device.

According to the inventive idea, the scenting device serves for scenting a vehicle interior of a vehicle and comprises at least one such substance container which holds a supply of an aromatic substance or is designed to do so. The scenting device comprises a feeding duct with which air is conducted to the at least one aromatic substance container. The air enriched with aromatic substance is conducted via a discharge duct out of the scenting device and can for example be directly fed to the vehicle interior. The respective aromatic substance container is assigned a scenting path, which branches off the feeding duct and for enriching the air with aromatic substance from the associated aromatic substance container leads through the associated aromatic substance container. In addition, the respective scenting path leads into the discharge duct. In addition, the scenting device comprises a bypass duct which branches off the feeding duct and bypasses the at least one aromatic substance container, with which air flowing through the feeding duct can be conducted past the aromatic substance containers. The bypass duct is assigned a bypass valve with which a volume flow through the bypass duct can be controlled. In addition, the respective scenting path is assigned a container valve for controlling a volume flow of the air through the associated scenting path. The scenting device additionally comprises the camshaft which comprises a bypass cam actuating the bypass valve and at least one container cam actuating the respective container valve.

The scenting device can be part of a ventilation device for ventilating the interior, in particular of an air conditioning system for air conditioning the interior of the vehicle.

The invention makes possible, furthermore, to precisely adjust the aromatic substance intensity with uniform overall volume flow or without influencing, in particular reducing the total volume flow in the feeding duct and/or discharge duct by way of the bypass function through the bypass duct and the control of the flow realised by the same. This leads to a stability of the scent intensity even with changing counter-pressures in the scenting device, which can occur for example because of changing air quantities in the scenting device or an associated air conditioning system. With the idea according to the invention, such back-pressures can thus be offset in particular with respect to the scent intensity.

The camshaft of the scenting device can be adjusted basically in any way, i.e. in particular rotated. For this purpose, an actuator can be provided which can be part of the scenting device.

Preferred are embodiments, in which each container valve is assigned a separate such container cam. This means that with the camshaft each of the valves can be actuated so that the relevant volume flow is adjustable via the common camshaft.

In principle, the bypass duct can lead out of the scenting device and be assigned another application for example of the associated vehicle.

Preferably, the bypass duct leads into the discharge duct. Thus, the total volume flow of the air through the feeding duct can correspond to the sum of the volume flows through the at least one aromatic substance container and the bypass duct, wherein this sum in turn corresponds to the volume flow through the discharge duct. In the result, the total volume flow through the feeding duct can correspond to the volume flow through the discharge duct.

In principle, the camshaft can be configured in such a manner that at least two of the cams are adjustable relative to one another.

Also conceivable are embodiments in which the cams of the camshaft have a fixed angular relationship relative to one another. As a consequence, each position of the camshaft is assigned a fixed position or a fixed angle of the respective cam. Accordingly, in the respective position of the camshaft, a corresponding proportion of the total volume flow can flow through the bypass duct and through the at least one such scenting path. Because of this, a simplified realisation of the adjustment is achieved by the precise adjustment of the volume flow through the bypass duct and the at least one scenting path.

Preferred are embodiments in which the cams of the camshaft interact with the valves in such a manner that the camshaft is adjustable between a bypass position, in which the total volume flow through the feeding duct flows through the bypass duct and at least one container position, in which the total volume flow through the feeding duct flows through such a scenting path. For this purpose, the scenting device is suitably configured. In particular, the cams and the valves are suitably matched to one another.

It is additionally preferred when the scenting device is configured in such a manner that the cams of the camshaft interact with the valves in such a manner that for each scenting path a container position of the camshaft in which the total volume flow flows through this scenting path is pre-set. This means that there is a position of the camshaft for each scenting path, in which the total volume flow through the feeding duct flows through this scenting path. Thus, there is at least one position of the camshaft, in which the total volume flow through the feeding duct is conducted past the at least one aromatic substance container and flows through the bypass duct. In addition, there is a position of the camshaft for each scenting path in which the total volume flow through the feeding duct flows through this scenting path.

Advantageous are embodiments in which the camshaft is adjustable in at least one intermediate position between the bypass position and at least one such container position. This means that in the intermediate position a proportion of the total volume flow through the feeding duct flows through the bypass duct and a proportion of the total volume flow through the feeding duct flows through the scenting path. It is also conceivable when intermediate positions are provided which are provided between two different such container positions. This means that at least one such intermediate position can exist in which a proportion of the total volume flow through the feeding duct flows through such a scenting path and a proportion of the total volume flow through the feeding duct flows through another such scenting path.

The feeding of air to the scenting device can be realised in principle in any way. For this purpose, external components of the scenting device, in particular of the associated vehicle, can be employed in particular.

Advantageous are embodiments in which the scenting device comprises a delivery device for delivering a delivery volume flow of air through the feeding duct. Here, the delivery volume flow delivered by the delivery device can correspond to the total volume flow through the feeding duct. The delivery device can in particular be designed as a pump or as a blower.

With regard to the scenting device, in particular with regard to the feeding duct and the discharge duct, the delivery device can be arranged in any way. This means that the delivery device can be arranged upstream or downstream of the feeding duct or of the discharge duct. Accordingly, the delivery device can deliver in a pumping or sucking manner.

In principle, the delivery device can provide merely a single output, i.e. can be switched on and switched off in particular without intermediate stages, or be configured accordingly. Thus, the delivery device can make available a constant delivery volume flow. Even with such a configuration of the delivery device, a significantly greater adjusting range or a more precise adjustment of the aromatic substance intensity can be achieved with the solution according to the invention than would be possible with the single output or the constant delivery volume flow of the delivery device.

Preferred are embodiments, in which the delivery device is configured in such a manner that the delivery volume flow is variable. This means that the delivery device cannot only be switched on and off but also be operated in operating modes in which the delivery volume flow assumes at least a value between a maximum delivery volume flow and no delivery volume flow or a minimum delivery volume flow. Here, the delivery device can be adjustable in particular in multiple stages or continuously. Thus, the aromatic substance intensity can be adjusted in particular even more precisely. In particular, a greater adjusting range of the aromatic substance intensity can thus be realised than would be possible with a pure adjustment of the delivery device.

Usually, in particular due to the design, such delivery device has an activation threshold. In the case of electrically operated delivery devices a minimum electric voltage as activation threshold is necessary for example so that the delivery device commences delivering. The activation threshold thus results in that the delivery device has to be supplied with a pre-set minimum power for it to commence delivering. As a consequence, the delivery device cannot provide a delivery volume flow that is as small as desirable, but at least a minimum delivery volume flow that is connected with the activation threshold. Without the idea according to the invention, this minimum delivery volume flow would then predetermine the minimum scent intensity. With the solution according to the invention, in particular through the bypass function, it is possible to adjust the minimum scent intensity more precisely and/or to be smaller.

The change of the delivery volume flow can be adjusted or controlled in particular by a corresponding output of the delivery device.

With preferred embodiments, the scenting device comprises at least two such aromatic substance containers. Accordingly, the scenting device comprises at least two such scenting paths, at least two such container valves and at least two such container cams.

The respective aromatic substance container can hold a supply of an aromatic substances of any type. It is conceivable, in particular, that the respective aromatic substance container contains a supply of another such aromatic substance.

Advantageous embodiments provide that at least one such aromatic substance container is designed as a replaceable cartridge or a flacon. Alternatively, at least one such aromatic substance container can comprise such a cartridge. Here, the associated supply of aromatic substance is contained in the cartridge so that a replacement and/or refilling of the aromatic substance are/is possible.

It is to be understood that besides the scenting device a vehicle having such a scenting device is also part of the scope of this invention. The vehicle in this case has an interior which is scented with the help of the scenting device. To this end, air flowing through the discharge duct of the scenting device is fed to the interior.

Advantageously, the vehicle comprises a control device which is configured in such a manner that it controls the scenting device. The control device in this case controls in particular the camshaft and/or the delivery device. Here it is conceivable that the control device is part of the scenting device.

Further important features and advantages of the invention are obtained from the subclaims, from the drawings and from the associated figure description by way of the drawings.

It is to be understood that the features mentioned above and still to be explained in the following cannot only be used in the respective combination stated but also in other combinations or by themselves without leaving the scope of the present invention.

Preferred exemplary embodiments of the invention are shown in the drawings and are explained in more detail in the following description, wherein same reference characters relate to same or similar or functionally same components.

BRIEF DESCRIPTION OF THE DRAWINGS

It shows, in each case schematically.

DETAILED DESCRIPTION

Figure 1:
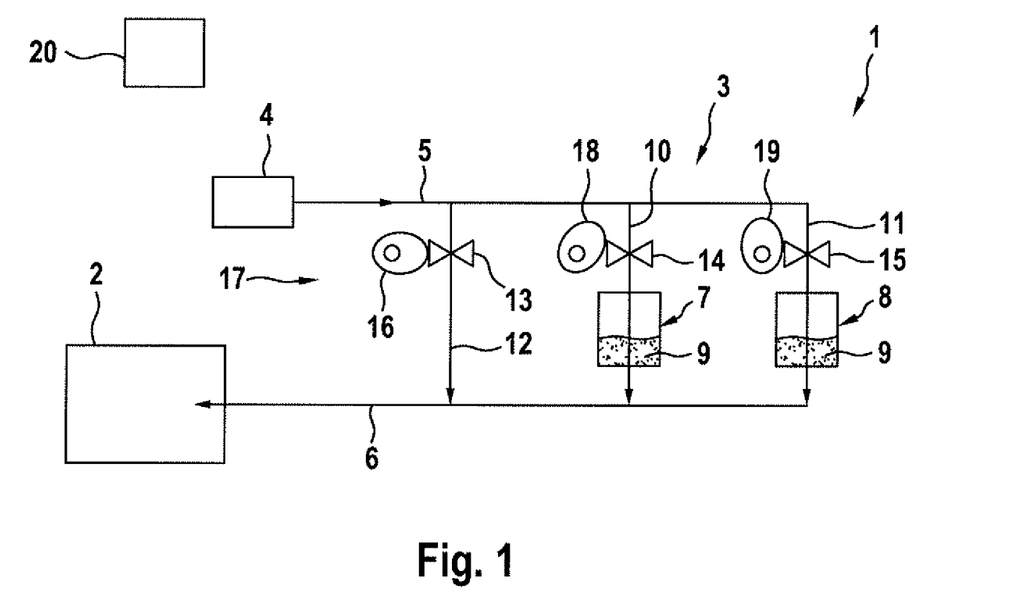
FIG. 1 a highly simplified representation of a vehicle with a scenting device in the manner of a circuit diagram, FIG. 2 a three-dimensional view of an example of the scenting device, FIG. 3 a partly sectioned three-dimensional view of a part of the scenting device from FIG. 2, FIG. 4 a section through the part of the scenting device shown in FIG. 3, FIG. 5 a diagram to explain the function of the scenting device.

A vehicle 1, as is shown highly simplified and in the manner of a circuit diagram in FIG. 1, comprises a vehicle interior 2 or interior 2 in brief. The interior 2 can be that for occupants of the vehicle 1 which are not shown. Furthermore, the vehicle 1 comprises a scenting device 3 for scenting the interior 2. The scenting device 3 comprises a delivery device 4 which feeds a delivery volume flow to a feeding duct 5, which in the shown example corresponds to the total volume flow of air through the feeding duct 5. The scenting device 3 additionally comprises a discharge duct 6 for discharging air from the scenting device 3, wherein the discharge duct 6 is fluidically connected to the interior 2, so that the air discharged with the discharge duct 6 from the scenting device 3 flows into the interior 2 and can thus scent the interior 2. Furthermore, the scenting device 3 comprises an aromatic substance container 7, 8, wherein in the shown example 2 such aromatic substance containers 7, 8, namely a first aromatic substance container 7 and a second aromatic substance container 8 are provided. The respective aromatic substance container 7, 8 holds a supply of an aromatic substance 9. For enriching the air to be fed to the interior 2 with aromatic substance 9, at least one proportion of the air flowing through the feeding duct 5 is conducted through at least one of the aromatic substance containers 7, 8 and subsequently fed to the discharge duct 6. For this purpose, the respective aromatic substance container 7, 8 is assigned a scenting path 10, 11. This means that the first aromatic substance container 7 is assigned a first scenting path 10 and the second aromatic substance container 8 is assigned a second scenting path 11. The first scenting path 10 branches off the feeding duct 5, results in the enriching of the branched-off air with aromatic substance 9 from the first aromatic substance container 7 through the first aromatic substance container 7 and leads into the discharge duct 6. The second scenting path 11 branches off the feeding duct 5 and results in the enriching of the branched-off air with aromatic substance 9 from the second aromatic substance container 8 through the second aromatic substance container 8 and leads into the discharge duct 6. In addition, a bypass duct 12 is provided which branches off the feeding duct 5 and conducts air flowing through the feeding duct 5 past the aromatic substance containers 7, 8 and leads into the discharge duct 6. This means that the bypass duct 12 conducts air flowing through the feeding duct 5 past the aromatic substance containers 7, 8 feeding it to the discharge duct 6. The bypass duct 12 is assigned a bypass valve 13 with which a volume flow of the air flowing through the bypass duct 12 is controlled. In addition, the respective scenting path 10, 11 is assigned an associated container valve 14, 15, with which a volume flow of the air flowing through the associated scenting path 10, 11 can be controlled. This means that with a first container valve 14 the volume flow of the air through the first scenting path 10 and thus through the first aromatic substance container 7 or the associated aromatic substance 9 and with a second container valve 15 the volume flow through the second scenting path 11 and thus through the second aromatic substance container 8 or the associated aromatic substance 9 can be controlled.

The bypass valve 13 is actuated with a bypass cam 16 of a camshaft 17, while the respective container valve 14, 15 is actuated with an associated container cam 18, 19 of the same camshaft 17. This means that the first container valve 14 is actuated by a first container cam 18 of the camshaft 17 while the second container valve 15 is actuated with a second container cam 19 of the camshaft 17.

Adjusting the camshaft 17 and thus the associated cams 16, 18, 19 and as a consequence the actuation of the valves 13, 14, 15 can take place by means of a control device 20, which can be part of the scenting device 3. The control device 20 additionally controls the delivery device 4, in particular an output of the delivery device 4 in such a manner that the delivery volume flow provided by the delivery device 4 corresponds to the total volume flow through the feeding duct 5, is adjustable in multiple stages or continuously. Together with the camshaft 17, a precise adjustment of the volume flow of the air flowing through the respective scenting path 10, 11 and through the bypass duct 12 can be realised here in a wide spectrum. This, the scenting of the interior 2 with a desired scent intensity of the respective aromatic substance 9 can be effected with high precision.

Figure 2:
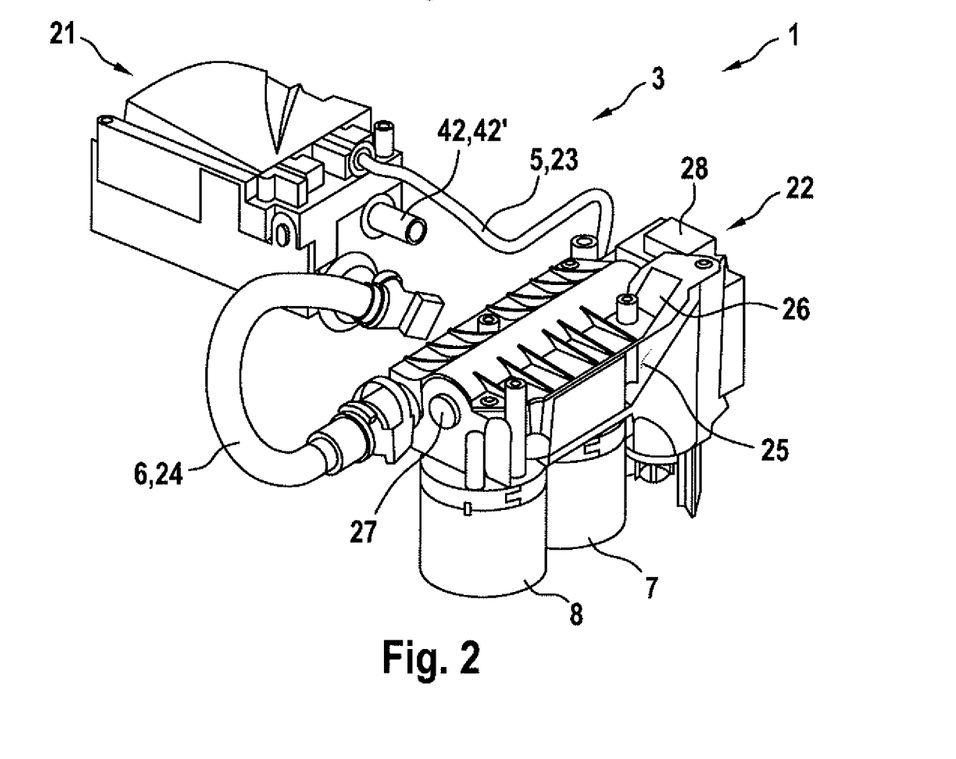

In FIG. 2 an example for such a scenting device 3 of the vehicle 1 is shown. The shown scenting device 3 comprises a delivery unit 21 in which the delivery device 4 which is not visible in FIG. 2 is integrated. The scenting device 3 additionally comprises a container unit 22 which comprises the aromatic substance container 7, 8. The delivery device 4 in this case is configured as a suction type purely exemplarily and sucks air in through the container unit 22 via a suction line 24. The air in this case flows into the container unit 22 through a suction opening 41 which in this case is provided on the actuator 28. The delivery unit 21 blows out the air that previously flowed through the container unit 22 and in particular contains aromatic substance, via an outlet line 42 provided on the container unit, which in the present case is designed as an outlet connector 42', wherein the outlet line 42 is fluidically connected to the vehicle interior 2 so that this in particular aromatic substance-containing air can flow into the vehicle interior 2. The actuator 28 is supplied and/or controlled in particular electrically by means of a supply line 23.

The container unit 22 comprises a housing 25 with a cover 26 closing the housing 25.

Figure 3:
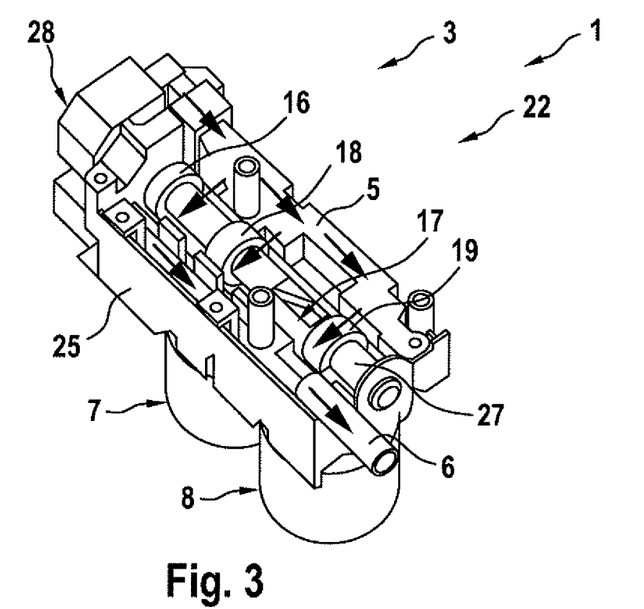
Figure 4:
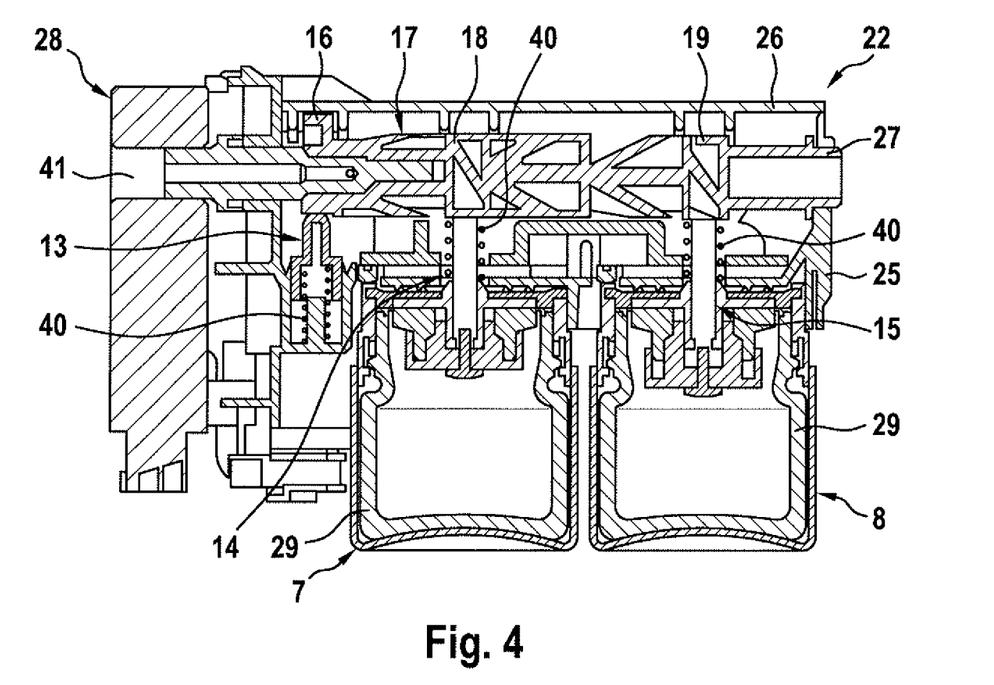

In FIG. 3, a three-dimensional view of the container unit 22 without cover 26 is visible, while in FIG. 4 a section through the container unit 22 is shown.

The camshaft 17, as is evident in particular from FIGS. 3 and 4, comprises a shaft 27, which is rotatably mounted in the housing 25. The cams 16, 18, 19 of the camshaft 17 are connected to the shaft 27 in each case in a rotationally fixed manner. The shaft 27 is rotated and thus adjusted by the actuator 28 of the scenting device 3 so that the actuator 28 also rotates and adjusts the cams 16, 18, 19. Because of this, the valves 13, 14, 15 are also adjusted by the actuator 28 via the cams 16, 18, 19. The actuator 28 is preferentially connected to the control device 20 in such a manner that the control device 20 can control the actuator 28.

As is evident in particular from FIG. 4, the respective valve 13, 14, 15 is provided with a spring 40 and thus spring-loaded. When the bypass valve 13 is loaded by the bypass cam 16, the spring force of the associated spring 40 is counteracted and the bypass duct 12 opened in such a manner that air can flow through the bypass duct 12. The same applies in the shown example to the container valves 14, 15. This means that under the action of the respective container cam 18, 19 the spring force of the associated spring 40 acting on the associated container valve 14, 15 is counteracted so that the associated scenting path 10, 11 can be flowed through by air.

From FIG. 4 it is evident that the respective aromatic substance container 7, 8 comprises a replaceable cartridge 29 which holds a supply of the associated aromatic substance 9. Thus, the respective cartridge 29 can be replaced if required for example for replacing and exchanging and/or refilling the aromatic substance 9. To this end, the respective aromatic substance container 7, 8 is detachably mounted on the container unit 22.

As is evident in particular from FIGS. 1, 3 and 4, the cams 16, 18, 19 of the camshaft 17 have a fixed angular relationship relative to one another, wherein they are orientated with respect to the shaft 27, at different angles. Through the rotation of the shaft 27, the bypass duct 12, the first scenting path 10 or the second scenting path 11 can be optionally opened here. Obviously, positions of the camshaft 7 in which the total volume flow of the air flowing through the feeding duct 5 partly flows through the bypass duct 12 and/or partly through the first scenting path 10 and/or partly through the second scenting path 11 are also conceivable.

Figure 5:
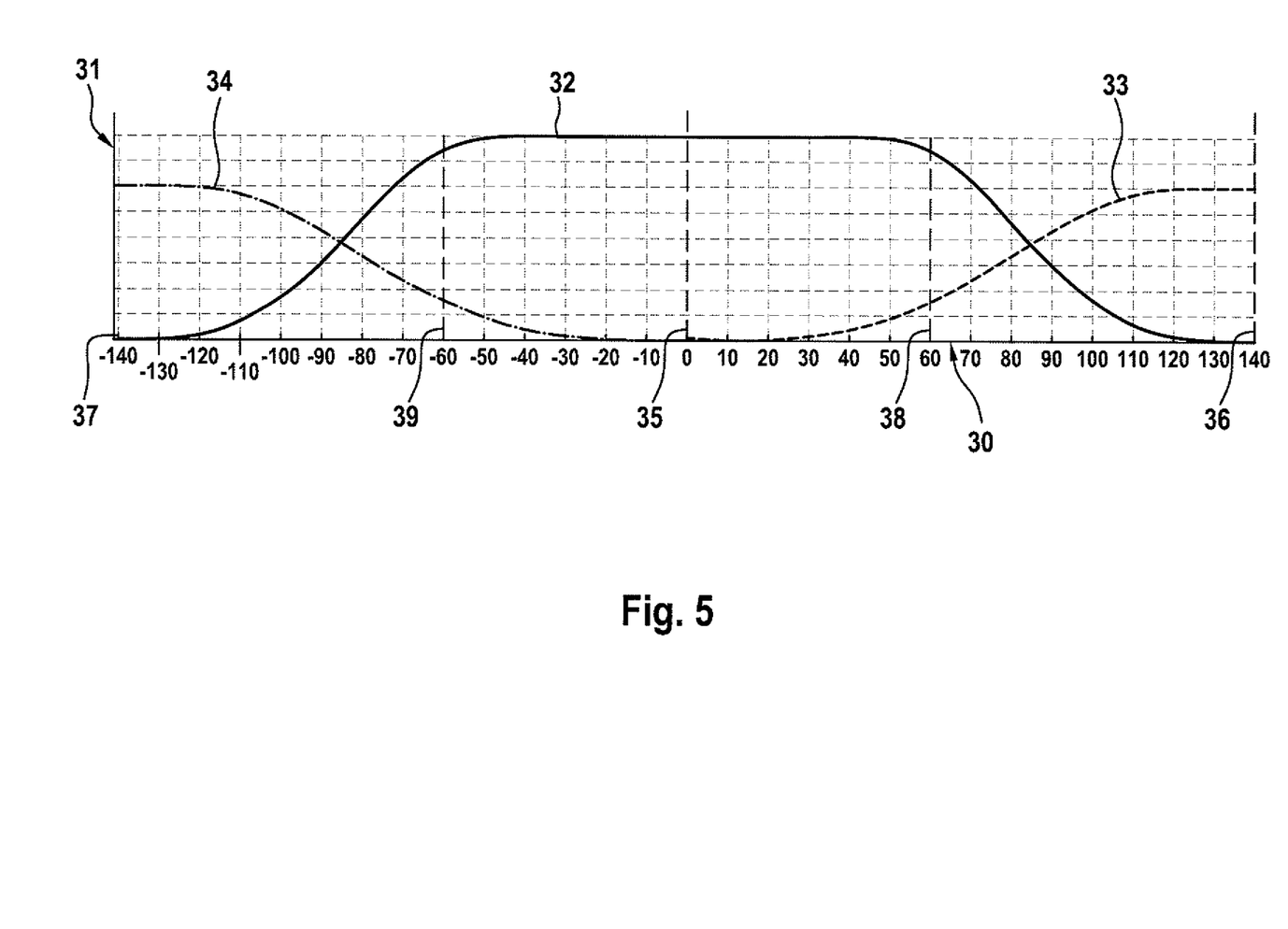

FIG. 5 shows a diagram, in which the flow of the air through the scenting paths 10, 11 and the bypass duct 12 as a function of the position of the camshaft 17 is shown. Here, an abscissa axis 30 of the diagram shows a curve of an angular position of the camshaft 17, whereas an ordinate axis 31 of the diagram shows a position of the respective valve 13, 14, 15. A valve position 32 of the bypass valve 13 is shown in FIG. 5 with a continuous line. A valve position 33 of the first container valve 14 is shown with a dashed line. A valve position 34 of the second container valve 15 is shown by a dash-dotted line. Accordingly, there is a bypass position 34 of the camshaft 17 in which the bypass valve 13 is fully open and the container valves 14, 15 are fully closed. In the bypass position 35, the total volume flow thus flows through the feeding duct 5 via the bypass duct 12 to the discharge duct 6. In addition, there are container positions 36, 37 of the camshaft 17, in which the total volume flow through the feeding duct 5 flows through one of the scenting paths 10, 11. Thus there exists a first container position 36 of the camshaft 17 in which the first container valve 14 is fully opened and the second container valve 15 and the bypass valve 13 are fully closed, so that the total volume flow through the feeding duct 5 flows through the first scenting path 10, is enriched with aromatic substance 9 in the first aromatic substance container 7 and enters the discharge duct 6. In addition there is a second container position 37 in which the total volume flow through the feeding duct 5 flows through the second scenting path 11, is enriched with aromatic substance 9 in the second aromatic substance container 8 and flows into the discharge duct 6. Numerous intermediate positions 38, 39 of the camshaft 17 are also present, in which the total volume flow through the feeding duct 5 partly flows through the bypass duct 12 and partly through one of the scenting paths 10, 11. In these intermediate positions 38, 39 the bypass valve 13 and the corresponding container valve 14, 15 are thus partly opened. In FIG. 5, two such intermediate positions 38, 39 are marked separately. In a first intermediate position 38, the bypass valve 13 and the first container valve 14 are partly opened whereas the second container valve 15 is fully closed so that the total volume flow through the feeding duct 5 is divided over the bypass duct 12 and the first scenting path 10. In a second intermediate position 39, the bypass valve 13 and the second container valve 15 are partly opened while the first container valve 14 is fully closed so that the total volume flow through the feeding duct 5 is divided over the bypass duct 12 and the second scenting path 11.

FIG. 5 shows that any further intermediate positions are also possible since the valves 13, 14, 15 and the cams 16, 18, 19 are continuously adjustable. Thus, a fine adjustment of the volume flow flowing through the respective scenting path 10, 11 and through the bypass duct 12 can be achieved. This can be further improved in that the delivery volume flow delivered by the delivery device 4, which in this case corresponds to the total volume flow through the feeding duct 5, is varied.

The invention claimed is:

1. A scenting device for scenting a vehicle interior, comprising:
   at least one aromatic substance container holding a supply of an aromatic substance;
   a feeding duct for feeding air to the at least one aromatic substance container;
   a discharge duct for discharging air enriched with the aromatic substance;
   at least one scenting path for enriching air with the aromatic substance from the at least one aromatic substance container, the at least one scenting path branching off from the feeding duct and leading through the at least one aromatic substance container and into the discharge duct;
   a bypass duct branching off from the feeding duct and bypassing the at least one aromatic substance container for conducting air flowing through the feeding duct past the at least one aromatic substance container;
   a bypass valve for controlling a volume flow of air flowing through the bypass duct;
   at least one container valve for controlling a volume flow through the at least one scenting path; and
   a camshaft including a bypass cam configured to actuate the bypass valve and at least one container cam configured to actuate the at least one container valve.

2. The scenting device according to claim 1, wherein the bypass duct leads into the discharge duct.

3. The scenting device according to claim 1, wherein the bypass cam and the at least one container cam have a fixed angular relationship relative to one another.

4. The scenting device according to claim 1, wherein the bypass cam interacts with the bypass valve and the at least one container cam interacts with the at least one container valves such that the camshaft is adjustable between a bypass position where a total volume flow through the feeding duct flows through the bypass duct, and at least one container position where the total volume flow through the feeding duct flows through the at least one scenting path.

5. The scenting device according to claim 4, wherein the total volume flow through the at least one scenting path in the at least one container position is pre-set.

6. The scenting device according to claim 4, wherein the camshaft is adjustable between the bypass position and the at least one container position when in at least one intermediate position.

7. The scenting device according to claim 1, further comprising a delivery device for delivering a delivery volume flow of air through the feeding duct.

8. The scenting device according to claim 7, wherein the delivery device is configured such a manner that the delivery volume flow is variable.

9. The scenting device according to claim 1, wherein the at least one aromatic substance container includes at least two aromatic substance containers.

10. The scenting device according to claim 1, wherein at least one of:
    the at least one aromatic substance container is configured as a replaceable cartridge; and
    the at least one aromatic substance container includes a replaceable cartridge.

11. A vehicle, comprising:
    an interior; and
    a scenting device for scenting the interior, the scenting device including:
        at least one aromatic substance container holding a supply of an aromatic substance;
        a feeding duct for feeding air to the at least one aromatic substance container;
        a discharge duct for discharging air enriched with the aromatic substance into the interior;
        at least one scenting path for enriching air with the aromatic substance from the at least one aromatic substance container, the at least one scenting path branching off from the feeding duct leading through the at least one aromatic substance container and into the discharge duct;
        a bypass duct branching off from the feeding duct and bypassing the at least one aromatic substance container for conducting air flowing through the feeding duct past the at least one aromatic substance container;
        a bypass valve for controlling a volume flow of air flowing through the bypass duct;
        at least one container valve for controlling a volume flow through the at least one scenting path; and
        a camshaft including a bypass cam configured to actuate the bypass valve and at least one container cam configured to actuate the at least one container valve.

12. The scenting device according to claim 11, wherein the bypass cam interacts with the bypass valve and the at least one container cam interacts with the at least one container valve such that the camshaft is adjustable between a bypass position where a total volume flow through the feeding duct flows through the bypass duct, and at least one container position where the total volume flow through the feeding duct flows through the at least one scenting path.

13. The scenting device according to claim 12, wherein the total volume flow through the at least one scenting path in the at least one container position is pre-set.

14. The scenting device according to claim 11, further comprising a delivery device for delivering a delivery volume flow of air through the feeding duct.

15. The scenting device according to claim 11, wherein at least one of:
    the at least one aromatic substance container is configured as a replaceable cartridge; and
    the at least one aromatic substance container includes a replaceable cartridge.

16. A scenting device for scenting a vehicle interior, comprising:
    a plurality of aromatic substance containers holding a supply of an aromatic substance;
    a feeding duct for feeding air to the plurality of aromatic substance containers;
    a discharge duct for discharging air enriched with the aromatic substance into a vehicle interior;
    a delivery device for delivering a delivery volume flow of air through the feeding duct, the delivery device configured such that the delivery volume flow is variable;
    a plurality of scenting paths for enriching air with the aromatic substance from an associated aromatic substance container of the plurality of aromatic substance containers, the plurality of scenting paths each branching off from the feeding duct leading through the associated aromatic substance container and into the discharge duct;
    a bypass duct branching off from the feeding duct and bypassing the plurality of aromatic substance containers for conducting air flowing through the feeding duct past the plurality of aromatic substance containers;
    a bypass valve for controlling a volume flow of air flowing through the bypass duct;

a plurality of container valves for controlling a volume flow through an associated scenting path of the plurality of scenting paths; and a camshaft including a bypass cam configured to actuate the bypass valve and a plurality of container cams each configured to actuate a respective container valve of the plurality of container valves.

17. The scenting device according to claim 16, wherein the bypass cam and the plurality of container cams have a fixed angular relationship relative to each other.

18. The scenting device according to claim 16, wherein the bypass cam interacts with the bypass valve and the plurality of container cams interact with the plurality of container valves such that the camshaft is adjustable between a bypass position where a total volume flow through the feeding duct flows through the bypass duct, and a plurality of container positions where the total volume flow through the feeding duct flows through the plurality of scenting paths.

19. The scenting device according to claim 18, wherein each of the plurality of container positions correspond to a respective scenting path of the plurality of scenting paths, wherein in the plurality of container positions the total volume flow through the feeding duct flows through the respective scenting path, and wherein each of the plurality of container positions are pre-set.

20. The scenting device according to claim 16, wherein at least one of:

at least one of the plurality of aromatic substance containers is configured as a replaceable cartridge; and at least one of the plurality of aromatic substance containers includes a replaceable cartridge.

* * * * *

UNITED STATES PATENT AND TRADEMARK OFFICE
CERTIFICATE OF CORRECTION

PATENT NO.         : 10,661,636 B2
APPLICATION NO.    : 15/878397
DATED              : May 26, 2020
INVENTOR(S)        : Bauer et al.

Page 1 of 1

It is certified that error appears in the above-identified patent and that said Letters Patent is hereby corrected as shown below:

In the Claims

At Column 9, Claim number 8, Line number 53, please remove "a manner".

Signed and Sealed this
Twenty-second Day of September, 2020

Andrei Iancu
*Director of the United States Patent and Trademark Office*